United States Patent [19]
Tanaka

[11] Patent Number: 4,601,050
[45] Date of Patent: Jul. 15, 1986

[54] METHOD OF TESTING CERAMIC ARTICLE

[75] Inventor: Shun-ichiro Tanaka, Yokohama, Japan

[73] Assignee: Kabushiki Kaisha Toshiba, Kawasaki, Japan

[21] Appl. No.: 615,272

[22] Filed: May 30, 1984

[30] Foreign Application Priority Data

May 31, 1983 [JP] Japan .................................. 58-96600

[51] Int. Cl.⁴ .............................................. G21K 3/00
[52] U.S. Cl. ...................................... 378/18; 378/156; 378/159
[58] Field of Search .......................... 378/156, 18, 159

[56] References Cited

FOREIGN PATENT DOCUMENTS 1005557 9/1965 United Kingdom ................ 378/156
1150193 4/1969 United Kingdom ................ 378/156

Primary Examiner—Craig E. Church
Attorney, Agent, or Firm—Cushman, Darby & Cushman

[57] ABSTRACT

A method of testing a ceramic article, comprising photographing a ceramic article by X-ray computed tomography in a state where at least one portion of the ceramic article is placed in a filling material having an X-ray absorption coefficient close to or less than that of the ceramic article in order to simplify the shape of a combination of the ceramic article and the filling material, thereby allowing precise and easy detection of microdefects in a ceramic article which has a complex shape.

8 Claims, 4 Drawing Figures

F I G. 3
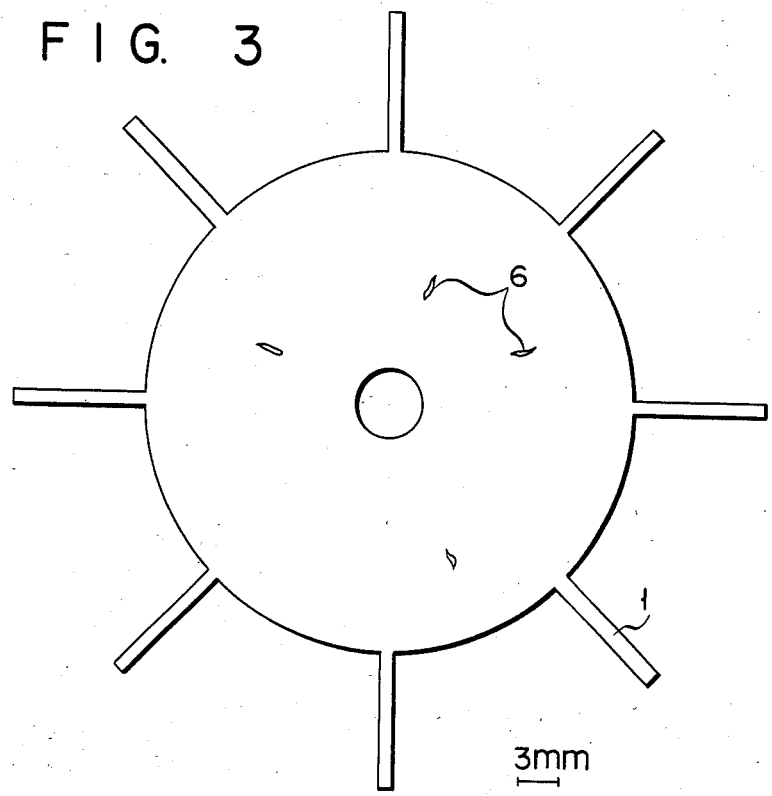
3mm
F I G. 4
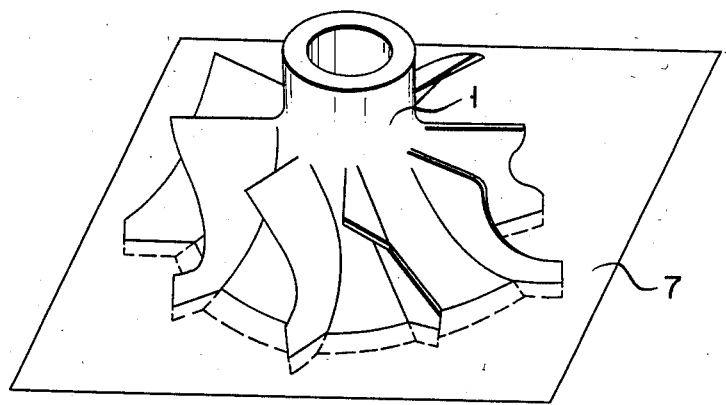

METHOD OF TESTING CERAMIC ARTICLE

BACKGROUND OF THE INVENTION

1. Field of the Invention

The present invention relates to a method of testing a ceramic article utilizing X-ray CT (computed tomography).

2. Description of the Prior Art

Ceramic articles have various advantages such as light weight, high mechanical strength, high corrosion resistance at high temperatures, and the like. With recent improvements in the quality of ceramic articles and developments in manufacturing methods thereof, studies are being made in many fields on the feasibility of replacing metals with ceramics.

However, ceramics are generally more brittle than metals and have microdefects which may lead to fracturing or damage to the articles consisting of such ceramics. In view of this, a demand has arisen for a method of nondestructively checking ceramic articles for microdefects which subsequently cause damage.

A nondestructive method utilizing transmitted X-rays is conventionally used for testing a metal article, especially a welded portion of a cast metal. However, ceramic articles to be tested include not only those of simple shapes such as plate-like or cylindrical ceramic articles but also those of complex shapes such as one-piece-shaped articles, e.g., turbo-charger rotors. When a ceramic article having such a complex shape is irradiated with transmitted X-rays, the level of noise is increased due to the complex profile and the correct discrimination of defects is difficult.

In the field of clinical medicine, X-ray CT (computed tomography) is used to obtain a tomograph of a living organism. It seems plausible to use this X-ray technique for testing ceramic articles. However, in this case, a false image, called an "artifact", is included in a tomograph of an object, such as a ceramic article, which has a high contrast and a more complex shape than a living organism. This "artifact" interferes with defect detection in a ceramic article. The "artifact" is a false image which appears when reconstructing a tomograph of a ceramic article based on data representing X-rays transmitted therethrough, and can therefore lead to erroneous detection of a normal portion of the ceramic article as a defect or vice versa.

SUMMARY OF THE INVENTION

The inventor of the present invention has made studies to solve the above problem and, on the basis of which, has found out that when a ceramic article of a complex shape is placed in a material having an X-ray absorption coefficient equivalent to that of the ceramic, the material fills any recesses in the ceramic article so that the overall object to be tested has a simple, apparent shape. Then, the object will have a uniform contrast, no artifact will be generated, and a CT image clearly displaying any present defects will be obtained.

The present invention has been established based on this finding and has as its object to provide a method of testing a ceramic article utilizing X-ray CT, which can provide a CT image without an artifact.

The method of testing a ceramic article, according to the present invention, comprises photographing the ceramic article by X-ray computed tomography in a state wherein the ceramic article is placed in a filling material having an X-ray absorption coefficient close to or less than that of the ceramic material of the ceramic article.

When medical CT is utilized, ceramic articles to be tested by the method of the present invention are suitably those which contain as major components elements having small X-ray absorption coefficients such as C, Mg, Al, Si, or B. The ceramic material may thus be $Al_2O_3$, $SiO_2$, SiC, $Si_3N_4$, MgO, BN, Sialon, or the like. If a high-energy X-ray source is used, a ceramic having a high X-ray absorption coefficient, such as $ZrO_2$, can be used.

The ceramic article to be tested by the method of the present invention can not only be a sintered ceramic material, such as a final product, but also an unsintered ceramic shaped body, such as an injection-molded body containing a synthetic resin as a binder, a cast-molded body, or a compact-molded body, or dewaxed or pre-sintered bodies thereof. Furthermore, the ceramic article is not limited to those consisting of only one type of ceramic material but can also include those consisting of a composite ceramic of two or more ceramic materials. The ceramic article can also consist of a composite material of such ceramic materials or a composite ceramic and a metal.

An X-ray CT apparatus to be used in the method of the present invention preferably has an X-ray source having a voltage of about 120 kV and a current of about 200 to 350 mA. When such an X-ray source is used, a resolution of about 400 $\mu$m can be obtained by intermittently radiating pulse X-rays of 1 to 7.5 msec duration at a pulse frequency of 300 to 600 times per rotation (360°) of the X-ray source around the ceramic article.

The filling material to be used in the method of the present invention has an X-ray mass absorption coefficient which is close to or less than that of the ceramic article. In the present invention, it is sufficient for the filling material to have an X-ray absorption coefficient greater than that of water. Preferably, its X-ray absorption coefficient should be 60% or more of that of the ceramic article. Such a filling material can be a liquid material such as silicone oil or water, a powder material such as a metal or ceramic powder, or a solid material such as a silicone rubber. When liquid, e.g., silicone oil is used as the filling material, the test of the ceramic article utilizing X-ray computed tomography is performed as follows. The ceramic article is placed in a container, which has a cylindrical body shape, and silicone oil is sealed therein. Then, the X-ray source and a detector are rotated for scanning about the axis of the container. When the filling material is a liquid, it can easily flow into the concaves, if any, of a ceramic article having a complicated shape. This is the advantage of a liquid filling material. When a powder material of a metal or a ceramic is used as the filling material, the test is performed in the same manner as described above. In this case, it is noted that the powder must be filled in the container in such a way that no spaces are formed between the ceramic material and the powder. When the filling material is a powder, it does not infiltrate into the ceramic article. Hence, it does not change the surface condition of the article. This is the advantage of a powder filling material. Alternatively, when a solid material such as a silicone rubber is used as the filling material, a pair of molds is formed by the silicone rubber so as to fit around the shape of the ceramic article. When testing, the ceramic article can be placed in these molds. In this case, only the complex shaped portion of the ceramic article can be placed in the molds, and the whole ceramic article need not be placed therein. Accordingly, it is important for the test that a combination of the ceramic article and the filling material fitted thereto has a simple shape. When the filling material is a solid one, it is easy to handle.

The filling material can be selected with regard to a value of the X-ray absorption coefficient of the ceramic article to be tested.

The table below shows densities X-ray absorption coefficients $\mu$ (1/cm) of various materials at X-ray source voltage of 120 kV (effective voltage: above 83 kV; $\lambda$: 0.15 Angstrom).

TABLE

|  | $\mu$ (1/cm) | air: $-1,000$ water: 0 |
| --- | --- | --- |
| Al | 0.554 | |
| Si | 0.501 | |
| C (graphite) | 0.349 | |
| Mg | 0.331 | |
| Fe | 4.565 | |
| Cu | 7.010 | |
| Ti | 1.778 | |
| Ni | 6.319 | |
| $Al_2O_3$ | 0.374 | |
| $SiO_2$ | 0.496 | |
| SiC | 0.632 | |
| $Si_3N_4$ | 0.629 | |
| MgO | 0.641 | |
| BN | 0.351 | |
| $Cr_2O_3$ | 1.980 | |
| $ZrO_2$ | 7.767 | |
| silicone oil | 0.2-0.4 | |
| silicone rubber | 0.2-0.4 | |
| $H_2O$ | 0.02 | |

It is seen from the above table that it is preferable if the filling material used for testing the ceramic article formed of $Al_2O_3$ is graphite powder, the filling material used for testing the ceramic article formed of $SiO_2$ is Si powder, and the filling material used for testing the ceramic article formed of $Si_3N_4$ is $Si_3N_4$ powder or silicone oil.

The combination of the ceramic article and the filling material has a simple shape when the above filling materials corresponding to the respective ceramic articles are used. When a cross-section of the ceramic material is photographed by X-ray computed tomography, the contrast is decreased and made uniform, and then a clear tomograph of the ceramic article without an artifact can be obtained. As a result, microdefects in a ceramic article having a complex shape can be precisely and easily detected.

BRIEF DESCRIPTION OF THE DRAWINGS

FIG. 3 is a view showing a reconstructed tomograph of the ceramic article; and

FIG. 4 is a view showing a position of a section of the ceramic article coresponding to the reconstructed tomograph thereof.

DETAILED DESCRIPTION OF THE PREFERRED EMBODIMENTS

The present invention will now be described by way of its Example.

EXAMPLE

A composition obtained by uniformly mixing 100 weight parts of polystyrene resin as a binder and 400 weight parts of $Si_3N_4$ powder was injection molded to provide an unsintered ceramic article 1 of a turbocharger rotor having a base diameter of 65 mm, a blade height of 25 mm, and 8 blades.

Figure 1:
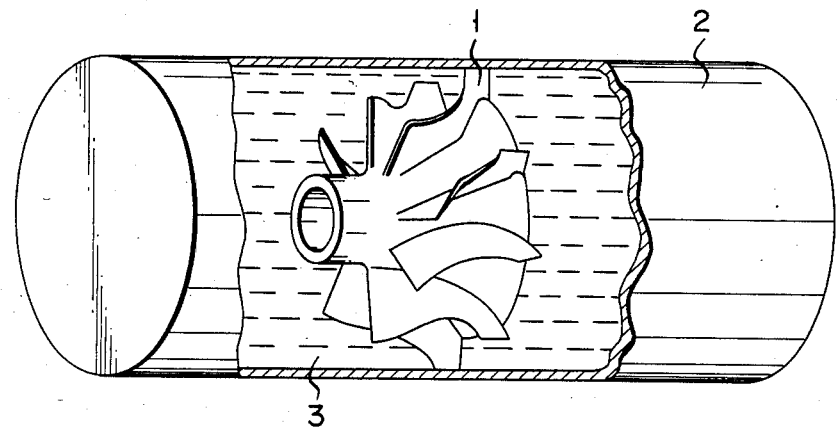
FIG. 1 is a view showing a ceramic article placed in silicone oil sealed in a container according to the method of the present invention.

The unsintered ceramic article (rotor) 1 thus obtained was placed in a cylindrical container 2 having a thickness of 2 mm, an inner diameter of 90 mm, and a length of 80 mm, as shown in FIG. 1. Silicone oil 3 (TSF-451; TOSHIBA SILICONE) was sealed in the container 2.

Figure 2:
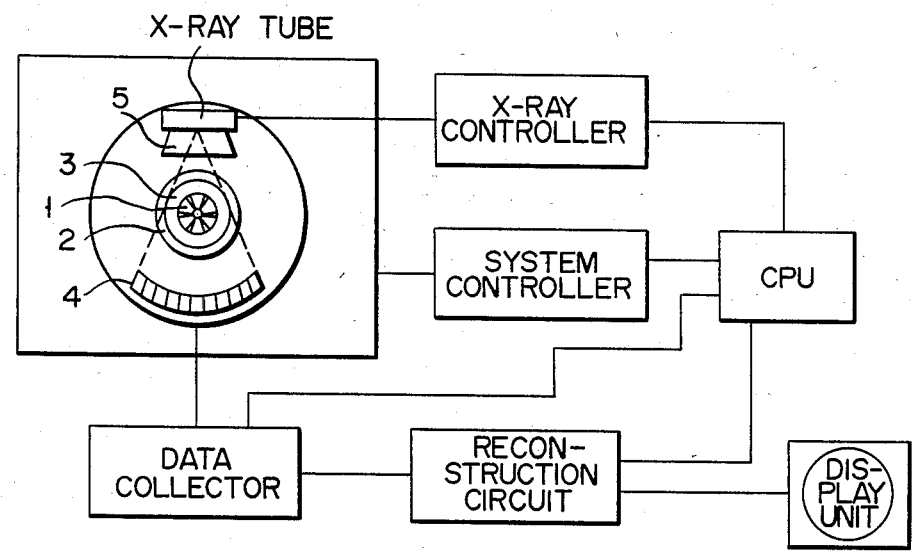
FIG. 2 is a schematic block diagram showing an arrangement of an X-ray computed tomography apparatus to be used in the method of the present invention.

Then, the cylindrical container 2 was fixed on a bed, and a total X-ray computed tomography apparatus (TCT 80A; TOSHIBA CORP.) was arranged as shown in FIG. 2. The X-ray computed tomography apparatus comprises an X-ray tube, an X-ray controller for controlling X-rays irradiated from the X-ray tube, an X-ray collimator 5 for shaping the X-rays irradiated from the X-ray tube into a fan beam, an X-ray detector 4 for converting to an electric signal an intensity of the X-rays which are transmitted through the ceramic article 1 and the silicone oil 3 in the container 2, a system controller for controlling the rotation or the like of the X-ray tube and the detector 4, a data collector for obtaining projection data by integrating an output from the X-ray detector, a reconstruction circuit for performing image reconstruction processing of the projection data from the X-ray detector, a CPU for performing data processing for each unit, and a display unit for displaying a CT image from the reconstruction circuit.

Using the X-ray computed tomograph apparatus having the arrangement described above, X-rays having a voltage of 120 kV, a current of 300 mA, and a pulse frequency of 600 pulses per cross section were irradiated for performing 360° scanning about the axis of the ceramic article. Then, a reconstructed image as shown in FIG. 3 was obtained. Micro-cracks 6 having a width of 0.5 mm and a length of about 2.0 mm could be detected from the reconstructed image. The reconstructed image of FIG. 3 shows a section of a gate portion of the rotor 1 taken along a plane 7 (FIG. 4) perpendicular to the axis of the rotor 1.

When $Si_3N_4$ was used as the filling material, an image was reconstructed which was better in quality than the image which had been obtained by using silicone oil as the filling material.

As described above, according to the present invention, microdefects in a ceramic material having a complex shape can be precisely and easily detected.

What is claimed is:

1. A method of testing a ceramic article comprising the steps of:
    placing at least one portion of said ceramic article in a filling material selected from the group consisting of silicone oil, silicone rubber, and ceramic powder, and
    photographing said ceramic article by X-ray computed tomography.

2. A method according to claim 1, wherein said ceramic article consists of a ceramic material which contains as a major component thereof an element selected from the group consisting of carbon, magnesium, aluminum and silicon.

3. A method according to claim 1, wherein said ceramic article consists of a ceramic material selected from the group consisting of a sintered ceramic material and an unsintered ceramic material.

4. A method according to claim 1, wherein said ceramic article consists of a composite ceramic of more than one ceramic material.

5. A method according to claim 1, wherein said ceramic article consists of a composite material of a metal and a ceramic material or composite ceramic.

6. A method according to claim 1, wherein the ceramic material is selected from the group consisting of aluminum oxide, aluminum nitride, silicon dioxide, silicon nitride, magnesium oxide, and Sialon.

7. A method according to claim 1, wherein the placing step includes the step of coaxially placing said ceramic article in a cylindrical container together with said filling material, wherein said filling material is in a liquid or powder form.

8. A method according to claim 1, wherein the placing step includes the step of placing said ceramic article in molds formed of silicone rubber.

* * * * *